United States Patent
Masson

(10) Patent No.: US 10,254,259 B2
(45) Date of Patent: Apr. 9, 2019

(54) METHOD, DEVICE, AND COMPUTER PROGRAM FOR LOCATING AN EMITTING SOURCE OF WHICH MEASUREMENTS OF EMISSION PROPAGATION AT LOCATIONS DIFFERENT FROM THAT OF THE EMITTING SOURCE CAN BE OBTAINED FROM THOSE LOCATIONS, LACKING SPACE PERCEPTION

(71) Applicant: INSTITUT PASTEUR, Paris (FR)

(72) Inventor: Jean-Baptiste Masson, Paris (FR)

(73) Assignee: INSTITUT PASTEUR, Paris (FR)

( * ) Notice: Subject to any disclaimer, the term of this patent is extended or adjusted under 35 U.S.C. 154(b) by 570 days.

(21) Appl. No.: 14/767,069

(22) PCT Filed: Mar. 14, 2014

(86) PCT No.: PCT/EP2014/055097
§ 371 (c)(1),
(2) Date: Aug. 11, 2015

(87) PCT Pub. No.: WO2014/140272
PCT Pub. Date: Sep. 18, 2014

(65) Prior Publication Data
US 2015/0377849 A1 Dec. 31, 2015

(30) Foreign Application Priority Data
Mar. 15, 2013 (EP) .................................. 13305306

(51) Int. Cl.
*G01N 31/00* (2006.01)
*G01N 33/00* (2006.01)
*G05B 15/02* (2006.01)

(52) U.S. Cl.
CPC ..... *G01N 33/0027* (2013.01); *G01N 33/0031* (2013.01); *G01N 33/0073* (2013.01); *G05B 15/02* (2013.01)

(58) Field of Classification Search
CPC .................................................. G01N 33/0027
See application file for complete search history.

(56) References Cited

U.S. PATENT DOCUMENTS

| | | | | |
|---|---|---|---|---|
| 5,068,597 A | * | 11/1991 | Silverstein | G01R 23/163 324/76.19 |
| 2005/0137804 A1 | * | 6/2005 | Permuy | G01V 1/362 702/14 |
| 2008/0010023 A1 | * | 1/2008 | Vergassola | G05D 1/0274 702/19 |

FOREIGN PATENT DOCUMENTS

EP      1 881 389      1/2008

OTHER PUBLICATIONS

Mathews, Z., et al., "Insect-Like Mapless Navigation Based on Head Direction Cells and Contextual Learning Using Chemo-Visual Sensors", Intelligent Robots and Systems IEEE/RSJ International Conference, (2009), XP31580624, pp. 2243-2250.

(Continued)

*Primary Examiner* — Hyun D Park
(74) *Attorney, Agent, or Firm* — Oblon, McClelland, Maier & Neustadt, L.L.P.

(57) ABSTRACT

A method and device for locating an emitting source of which measurements of emission propagation at locations different from that of the emitting source can be obtained from those locations, lacking space perception, using a sensor mobile along a self-generated path. After having obtained an emission propagation measurement from the mobile sensor at the mobile sensor location, a free energy variation for moving the sensor from its current location to each of plural possible next locations of the mobile sensor is (Continued)

computed, the free energy being computed as a function of a standardized projected probability field of the location of the diffusing source based on previous emission propagation measurements obtained along the self-generated path. A minimum free energy variation value amongst the computed free energy variations is determined and the location associated with the determined minimum free energy variation is identified as being the next location of the sensor.

14 Claims, 3 Drawing Sheets

(56) References Cited

OTHER PUBLICATIONS

Zhang, S., et al., "Effectiveness of Infotaxis Algorithm for Searching in Dilute Conditions", Chinese Control Conference, (2012), XP32289260, pp. 5048-5053.

Compton, D., "Application of an Olfactory Data-Preprocessing Algorithm to Chemotactic Robotic Navigation", Journal of Young Investigators, (2008), XP7922131, (Total pp. 5).

International Search Report dated Jun. 30, 2014 in PCT/EP2014/055097 Filed Mar. 14, 2014.

* cited by examiner

METHOD, DEVICE, AND COMPUTER PROGRAM FOR LOCATING AN EMITTING SOURCE OF WHICH MEASUREMENTS OF EMISSION PROPAGATION AT LOCATIONS DIFFERENT FROM THAT OF THE EMITTING SOURCE CAN BE OBTAINED FROM THOSE LOCATIONS, LACKING SPACE PERCEPTION

FIELD OF THE INVENTION

The present invention relates generally to methods and systems for locating emitting sources and more specifically to a method, a system, and a computer program for locating an emitting source of which measurements of emission propagation at locations different from that of the emitting source can be obtained from those locations, lacking space perception.

BACKGROUND OF THE INVENTION

While insects are able to navigate in turbulent streams to find their mates or food from sparse pheromone or odor detection, even in case of poor space perception for some of them, machines face difficulties in handling such a problem despite the needs e.g., locating drugs, chemical leaks, explosives, and mines. Semiconductor gas-sensors are able to detect the presence or absence of specific odorous substances and to determine their concentration. However, locating the sources has to take into account the environment and particularly the air or liquid flow in which the odorous substance diffuses in a chaotic way.

Most of the robots equipped with an odor sensor use the local concentration gradient of an odorous substance to determine locally the direction of its source, referred to as chemotactic search strategy. However, chemotactic search strategies based on local concentration gradients require concentration to be sufficiently high so that its average difference measured at two nearby locations is larger than typical fluctuations. The signal-to-noise ratio depends of course on the averaging time and might be improved by waiting. However, average concentration may be decaying rapidly e.g., exponentially, with the distance away from the source and in this weak signal-to-noise (dilute) case waiting becomes worse than exploratory motion. As an illustration, FIG. 1 depicts an example of an environment where an odorous substance is diffused within the atmosphere and where odorous substance concentration cannot be used locally to determine the odorous substance source.

Chemotaxis requires a reliable measurement of local gradients. This is not feasible for robots located far away from the source and severely limits the range of application of automated source localization by robots. Existing chemotaxic robots might take several minutes to locate a source a few meters away.

Therefore, there is a need to provide a method and systems for solving the challenge of locating an emitting source, e.g. locating particle or molecule sources or heat sources in a dilute environment, in particular for the design of sniffers or robots that track chemicals emitted by drugs, chemical leaks, explosives and mines.

To solve these issues, there is provided an efficient method, device, and computer program to search for an emitting source in a turbulent flow, lacking space perception and cognitive and/or probabilistic maps.

SUMMARY OF THE INVENTION

Faced with these constraints, the inventors provide a method, a device, and a computer program for locating an emitting source of which measurements of emission propagation at locations different from that of the emitting source can be obtained from those locations, in a highly variable environment, lacking space perception.

It is a broad object of the invention to remedy the shortcomings of the prior art as described above.

According to a first aspect of the invention there is provided a method for locating an emitting source of which a measurement of emission propagation at a different location from that of the emitting source can be obtained from that different location, in a searching space, lacking space perception, using a mobile sensor configured to obtain emission propagation measurements, the sensor being mobile along a self-generated path, the method comprising the steps of, obtaining an emission propagation measurement from the mobile sensor at the mobile sensor location;

for a plurality of possible next locations of the mobile sensor, computing a free energy variation for moving the sensor from its current location to each of the plurality of possible next locations, the free energy being computed as a function of a standardized projected probability field of the location of the diffusing source based on previous emission propagation measurements obtained along the self-generated path;

determining a minimum free energy variation value amongst the computed free energy variations; and identifying the location associated with the determined minimum free energy variation as being the next location of the mobile sensor.

Accordingly, the invention allows an emitting source such as a particle or molecule source or a heat source to be located in a dilute environment by a system having limited computing resources and lacking space perception and cognitive and/or probabilistic maps.

In an embodiment, the free energy variation is computed as a function of a first element that favors exploration of the searching space and as a function of a second element that favors exploitation of previous emission propagation measurements obtained along the self-generated path, the first and second elements being weighted in relation to each other.

In a particular embodiment, the method further comprises a step of determining whether the current sensor location or the next location of the mobile sensor corresponds to the location of the emitting source.

The steps of obtaining an emission propagation measurement, computing a free energy variation, determining a minimum free energy variation value, identifying the next location of the mobile sensor, and determining whether the current sensor location or the next location of the mobile sensor corresponds to the location of the emitting source are advantageously repeated until the location of the emitting source is located.

In a particular embodiment, the method further comprises a step of comparing the determined minimum free energy variation value with a predetermined threshold, the next location of the mobile sensor being identified as the location associated with the determined minimum free energy variation or as the current sensor location as a function of the result of the comparison.

In a particular embodiment, the method further comprises a step of storing the obtained emission propagation measurement in memory along with the current mobile sensor location.

In a particular embodiment, the method further comprises a step of moving the mobile sensor to the identified next location of the mobile sensor.

In a particular embodiment, a measurement of emission propagation characterizes detecting or not detecting emission of the emitting source.

According to a particular embodiment, the standardized projected probability field of the location of the diffusing source, representing the probability $P_t^M(\vec{r}_0|\Theta_t)$ that the emitting source is located at location $\vec{r}_0$, knowing path $\Theta_t$, can be expressed with the following formula:

$$P_t^M(\vec{r}_0 \mid \Theta_t) = \frac{e^{-\frac{\|\vec{r}_0 - \vec{r}_G\|^2}{\lambda_G^2}} \left(1 - \frac{1}{N_M} \sum_{j=N_t-N_M+1}^{N_t} e^{-\frac{\|\vec{r}_0 - \vec{r}_j\|^2}{\lambda_u^2}}\right)}{Z_t}$$

where $\vec{r}_G$ represents a damped mass center of previous locations where emission of the emitting source has been detected and $\lambda_G$ represents a scale associated with a Gaussian term approximating terms associated with detection of emission of the emitting source;

$\vec{r}_j$ represents the locations of the searching system sensor where emission of the emitting source has not been detected;

$N_M$ is the number of locations where measurements have been obtained;

$\lambda_u$ represents a scale of a Gaussian term approximating terms associated with absence of detection of emission of the emitting source; and $Z_t$ is a normalization constant.

In an embodiment, the step of obtaining an emission propagation measurement from the mobile sensor at the mobile sensor location further comprises the step of obtaining at least an emission propagation measurement from at least a second mobile sensor, different from the mobile sensor, at the location of the at least a second mobile sensor, the at least a second mobile sensor being configured to obtain emission propagation measurements, the at least a second mobile sensor being mobile along at least a second self-generated path, the free energy being computed as a function of the standardized projected probability field of the location of the diffusing source based on previous emission propagation measurements obtained along the self-generated path and on at least a previous emission propagation measurement obtained along the at least a second self-generated path.

In an embodiment, the standardized projected probability field of the location of the diffusing source, representing the probability $P_t^M(\vec{r}_0|\Theta_t)$ that the emitting source is located at location $\vec{r}_0$, knowing path $\Theta_t$, can be expressed with the following formula:

$$P_t^M(\vec{r}_0 \mid \Theta_t) = \frac{e^{-\frac{\|\vec{r}_0 - \vec{r}_G^{N_s}\|^2}{\lambda_G^2}} \left(-\frac{1}{N_M} \sum_{k=1}^{N_S} \sum_{j=N_t-\left[\frac{(N_M+1)}{N_S}\right]}^{N_S} e^{-\frac{\|\vec{r}_0 - \vec{r}_j^k\|^2}{\lambda_u^2}}\right)}{Z_t}$$

where $\vec{r}_G^{N_s}$ represents a damped mass center of previous locations where emission of the emitting source has been detected by the mobile sensor and the at least a second mobile sensor and $\lambda_G$ represents a scale associated with a Gaussian term approximating terms associated with detection of emission of the emitting source;

$\vec{r}_j^k$ represents the locations of a searching system sensor having index k where emission of the emitting source has not been detected;

$N_M$ is the number of locations where measurements have been obtained;

$\lambda_u$ represents a scale of a Gaussian term approximating terms associated with absence of detection of emission of the emitting source; and $Z_t$ is a normalization constant.

The emitting source may be a source of particles, molecules, or fragments of molecules, a heat source, or a source of data (the sensor being responsive to data patterns).

A second aspect of the invention provides a computer-readable storage medium storing instructions of a computer program for implementing the method in accordance with any embodiment of the first aspect of the invention.

A third aspect of the invention provides an apparatus or a set of apparatus comprising means adapted for carrying out each step of the method in accordance with any embodiment of the first aspect of the invention.

In an embodiment, the apparatus or the set of apparatus further comprises first means embedding said mobile sensor, said first means being mobile in said search space, and second means for computing the free energy variation, determining a minimum free energy variation value, and identifying the next location of the mobile sensor, the first and second means comprising means for exchanging data with each other.

Since the present invention can be implemented in software, the present invention can be embodied as computer readable code for provision to a programmable apparatus on any suitable carrier medium. A tangible carrier medium may comprise a storage medium such as a floppy disk, a CD-ROM, a hard disk drive, a magnetic tape device or a solid state memory device and the like. A transient carrier medium may include a signal such as an electrical signal, an electronic signal, an optical signal, an acoustic signal, a magnetic signal or an electromagnetic signal, e.g. a microwave or RF signal.

BRIEF DESCRIPTION OF THE DRAWINGS

Further advantages of the present invention will become apparent to those skilled in the art upon examination of the drawings and detailed description. It is intended that any additional advantages be incorporated herein.

Embodiments of the invention will now be described, by way of example only, and with reference to the following drawings in which:

FIG. 4, comprising

DETAILED DESCRIPTION OF EMBODIMENTS OF THE INVENTION

According to a particular embodiment, an efficient method, device, and computer program is provided to search for an emitting source in a turbulent flow, lacking space perception and cognitive and/or or probabilistic maps. The method, device, and computer program allow effective searches, in complex varying environments, with limited access to cues, by using a searching system having limited space processing capacities. The emitting source can be, for example, a source of particles, molecules, or fragments of molecules, a heat source, or any other source of which measurements of emission propagation at locations different from that of the emitting source can be obtained from those locations. The emitting source can also be a source of data or a source of errors in a communication network.

According to an embodiment, the searching system comprises a processing device, a mobile sensor, and moving means such as motorized wheels. All the elements of the searching system can be integrated in one moving apparatus, like an active mobile robot (that is to say an "intelligent" mobile robot), or can be integrated as two or more apparatus communicatively coupled. For the sake of illustration, the searching system may comprise a static computer, for example of the PC (Personal Computer) type, provided with a communication interface, and a passive mobile robot (that is to say a remotely controlled mobile robot) comprising a sensor, a communication interface that is compatible with that of the computer, and motorized wheels controlled by the computer. The communication interfaces may comply with any communication standard, preferably a wireless communication standard such as the one known as ISO/CEI 8802-11. The active or passive mobile robot can move along a self-generated path, with or without user-defined constraints, to locate the diffusing source.

Figure 1:
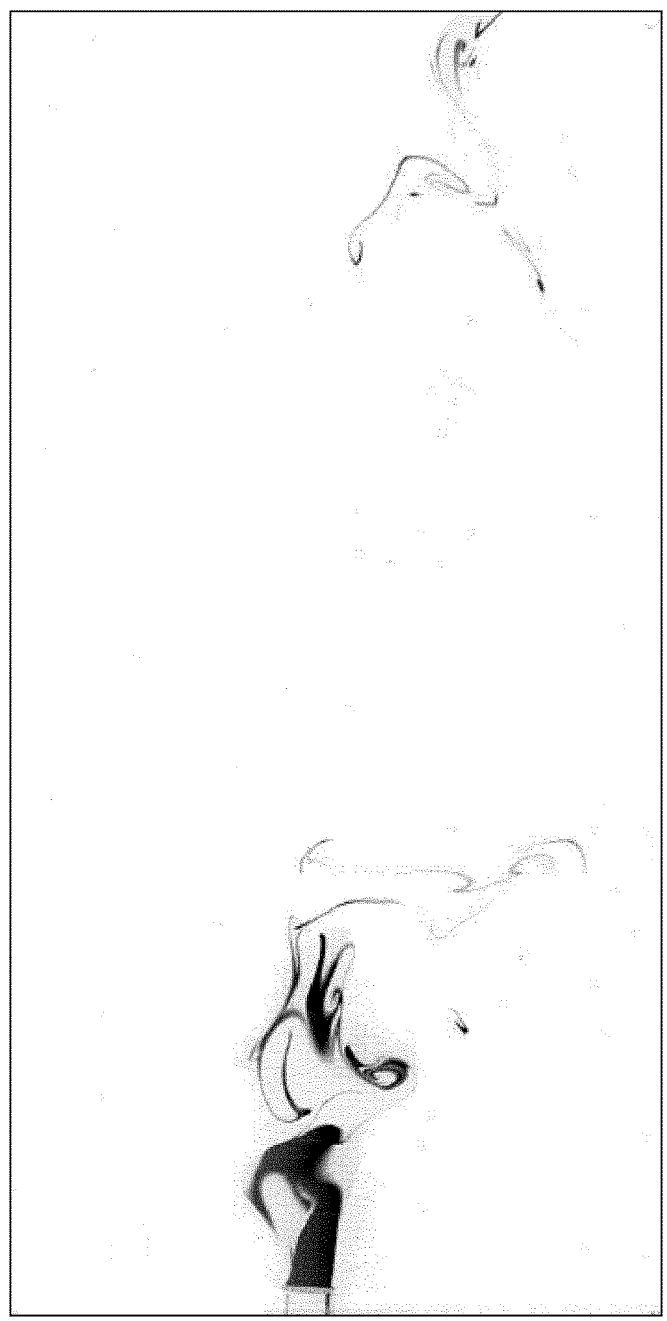
FIG. 1 illustrates an example of an environment where an odorous substance is diffused within the atmosphere and where odorous substance concentration cannot be used locally to determine the odorous substance source.
Figure 2:
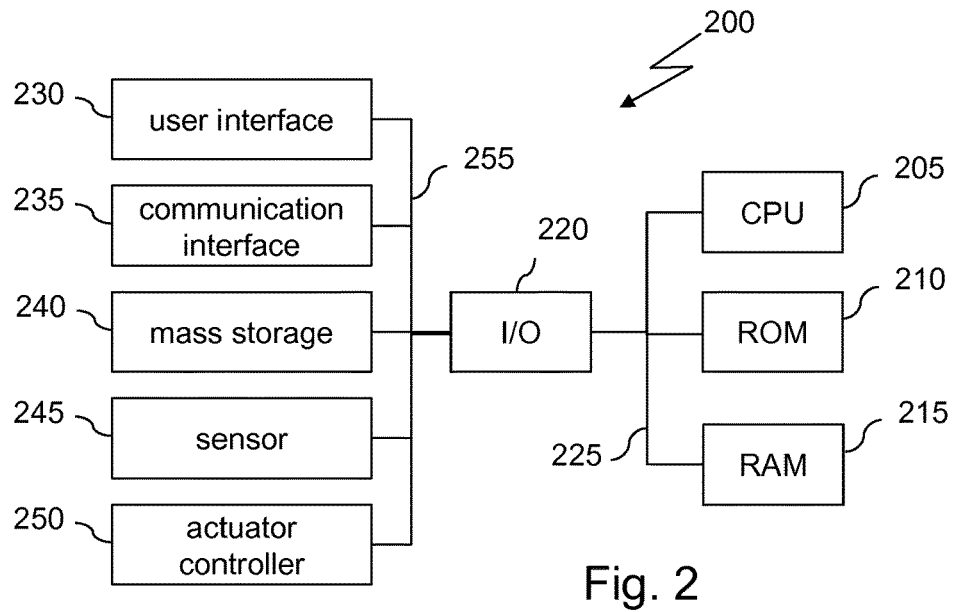
FIG. 2 illustrates an example of the architecture of a searching system according to a particular embodiment.

FIG. 2 illustrates an example of the architecture of a searching system 200. As shown, the searching system 200 comprises a central processing unit (CPU) 205, a Read-Only Memory (ROM) 210, a Random Access Memory (RAM) 215, and an input/output (I/O) subsystem 220, all of them being connected to a system bus 225. The I/O subsystem 220 may include one or more controllers for input/output devices such as user interface 230 (which may comprise a keyboard, a cursor control device, and a display device), communication interface 235 (which can be of wire or wireless type), mass storage device 240, at least one sensor 245 for remotely obtaining emission propagation measurements of the emitting sources searched for, and actuator controller 250 for controlling displacements of the searching system (or at least of the sensor 245).

Depending upon the application of the searching system 200, one or more further I/O devices may be connected to the I/O subsystem 220. Typically, the hardware system 200 is controlled by an operating system that can be stored in ROM 210 or in mass storage device 245, which in turn controls various tools and applications that are generally loaded in RAM 215.

The searching system may include several types of sensors to localize several kinds of emitting sources and/or to analyze particular features of the environment e.g., detecting obstacles.

Some of the elements of the searching system such as CPU 205, ROM 210, RAM 215, I/O subsystem 220, all of them being connected to a system bus 225, user interface 230, communication interface 235, and/or mass storage device 240 may be part of a generic computer device, handheld device, or any kind of computer device.

It should be noted that according to particular applications, the active or passive mobile robot can be a virtual mobile robot, for example a virtual robot allowing a data source or an error source in a communication network to be searched for. In such a case, the sensors to be used are preferably sensors that are responsive to data patterns.

According to a particular embodiment, the searching system is based on the use of the projection of a probability of the emitting source position into a standardized form, to avoid the need of advanced space perception, and on the evaluation by the searching system (of which the mobile sensor position is known from uncorrected noisy cueless path integration) of a free energy that is minimized in order to find the right path to the source. A parameter referred to as the "internal temperature" allows an efficient balance between exploration of the search space and exploitation of information already obtained.

Figure 3:
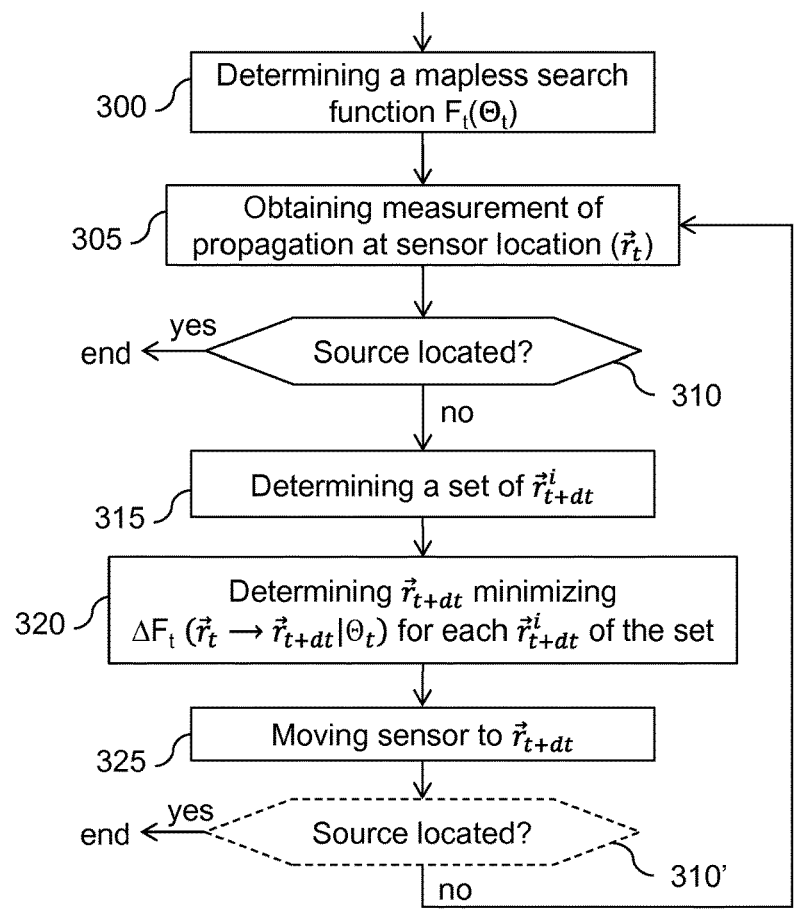
FIG. 3 illustrates steps of an algorithm to search for an emitting source of which measurements of emission propagation at locations different from that of the emitting source can be obtained from those locations, in a highly variable environment, lacking space perception, according to an embodiment.

FIG. 3 illustrates steps of an algorithm to search for an emitting source of which measurements of emission propagation at locations different from that of the emitting source can be obtained from those locations, in a highly variable environment, lacking space perception, according to an embodiment.

A first step (step 300) aims at determining a mapless search function $F_t(\Theta_t)$ representing a free energy that is to be minimized in order to find the right path to the source. An example of such a mapless search function is described herein below.

In a next step, a measurement of emission propagation related to the emitting source, at sensor location, is obtained. Such a measurement is typically a value, preferably a normalized value, for example a value varying from zero to one hundred, or a binary value, for example a binary value of which the value zero indicates that no emission propagation characteristic of the emitting source has been detected and the value one indicates that an emission propagation characteristic of the emitting source has been detected. It is to be noted that a binary value may be obtained from another type of value by using appropriate thresholds.

Next, according to a particular embodiment, a test is performed to determine whether or not the emitting source is located at sensor location $\vec{r}_t$ (step 310). Such a test can be performed, for example, by comparing the measured value with a threshold or by comparing a detection rate with a threshold.

Once a measurement of emission propagation related to the emitting source, at sensor location $\vec{r}_t$, has been obtained, a set of next possible sensor locations $\vec{r}_{t+dt}^{\,i}$ is determined (step 315). According to a particular embodiment, a set of next possible sensor relative locations are predetermined. For the sake of illustration, such a set of next possible sensor relative locations can be set as follows:

$$\vec{r}_{t+dt}^{\,1}(x_{\vec{r}_t}+1, y_{\vec{r}_t})$$

$$\vec{r}_{t+dt}^{\,2}(x_{\vec{r}_t}-1, y_{\vec{r}_t})$$

$\vec{r}_{t+dt}^{3}(x_{\vec{r}_t}, y_{\vec{r}_t}+1)$ $\vec{r}_{t+dt}^{4}(x_{\vec{r}_t}, y_{\vec{r}_t}-1)$ $\vec{r}_{t+dt}^{5}(x_{\vec{r}_t}+1, y_{\vec{r}_t}+1)$ $\vec{r}_{t+dt}^{6}(x_{\vec{r}_t}-1, y_{\vec{r}_t}+1)$ $\vec{r}_{t+dt}^{7}(x_{\vec{r}_t}+1, y_{\vec{r}_t}+1)$ $\vec{r}_{t+dt}^{8}(x_{\vec{r}_t}-1, y_{\vec{r}_t}-1)$ Next, a variation $\Delta F_t$ of the free energy as defined by the predetermined mapless search function $F_t(\Theta_t)$ between sensor location $\vec{r}_t$ and each of the next possible sensor locations $\vec{r}_{t+dt}^{i}$ is computed. The result having the minimum value is selected to determine the next sensor location $\vec{r}_{t+dt}$ (step 320).

According to a particular embodiment, the sensor may stay at its previous location $\vec{r}_t$ if, for example, the minimum variation $\Delta F_t$ of the free energy exceeds a predetermined threshold.

After having being determined, the sensor is moved to the next sensor location $\vec{r}_{t+dt}$ (step 325) and the algorithm is branched to step 305 to obtain a new measurement of emission propagation related to the emitting source, at a sensor location, and to repeat the previous described steps until the emitting source is reached. The obtained measurement of emission propagation is advantageously memorized along with current sensor location $\vec{r}_t$ to be later used for determining a direction to follow.

According to a particular embodiment, test 310 performed to determine whether or not the emitting source is located at sensor location $\vec{r}_t$ may be replaced by test 310' that aims at determining whether or not the emitting source is located at location $\vec{r}_{t+dt}$. Such a test may consist in comparing the value of $F_{t+dt}(\Theta_t)$ with a predetermined threshold. As described herein above, function $F_t(\Theta_t)$ can be chosen so that $F_{t+dt}(\Theta_t)=1$ if the source is at location $\vec{r}_{t+dt}$. Such a test may also be based on another type of measurements.

As described above, the searching system moves along a self-generated path denoted $\Theta_t$ (with or without user-defined constraints) and, at each iterating step, determines a direction to follow based on the events experienced at previous location of path $\Theta_t$. The searching system accesses its position from uncorrected path integration and is considered to evolve in a cue-limited environment preventing an accurate correction of its position. According to this particular embodiment, information bearing events are based on measurements of emission propagation of the emitting source at the sensor location. For the sake of example, it can be based on either detections of particles (rare local events) or the absence of detection of particles (frequent less localized events). Measurements of emission propagation can be compared to one or more thresholds, for example if the measurements represent particle density, to result in detections or absences of detection.

It is to be noted that the environment may be characterized by a function denoted $R(\vec{r}|\vec{r}_0)$ representing the rate of detection, which gives a rate of detection at location $\vec{r}$ when the source is located at location $\vec{r}_0$. A simplified model of such a function $R(\vec{r}|\vec{r}_0)$ can be, for example, a simple Gaussian function. In the case where the diffusing source is a particle diffusing source in the air, the exact expression reads as follows:

$$R(\vec{r}|\vec{r}_0) = \frac{R}{\ln\left(\frac{\lambda}{a}\right)} e^{-\left(\frac{(y-y_0)V}{2D}\right)} K_0\left(\frac{|\vec{r}-\vec{r}_0|}{\lambda}\right)$$

where $\tau$ and R represent the lifetime of emitted particles and their emission rate, respectively;

$\vec{V}$ represents a mean wind in the environment;

a is the characteristic length of the particle detector;

$K_0$ is the modified Bessel function of order zero;

(y and $y_0$) represents where the wind was taken to blow in the y direction and $y_0$ is the y-coordinate of the diffusing source; and $\lambda$ is defined as follows:

$$\lambda = \sqrt{\frac{D\tau}{1+\frac{V^2\tau}{4D}}}$$

where D represents the coefficient of diffusion of the particles.

The absence of complex space perception prevents the direct decoding by inference of the information stored in the path $\Theta_t$ using Bayesian inference. Hence, all terms involved in the path choosing mechanism have to be expressed in a standardized form to be computed without the complete expression of the time varying probability of finding the source at a particular location. The following standardized projected probability can be used, $$P_t^M(\vec{r}_0|\Theta_t) = \frac{e^{\frac{\|\vec{r}_0-\vec{r}_G\|^2}{\lambda_G^2}}\left(1-\frac{1}{N_M}\sum_{j=N_t-N_M+1}^{N_t} e^{\frac{\|\vec{r}_0-\vec{r}_j\|^2}{\lambda_u^2}}\right)}{Z_t}$$

where $P_t^M(\vec{r}_0|\Theta_t)$ is the probability that the emitting source is located in $\vec{r}_0$ knowing path $\Theta_t$, $\vec{r}_G$ represents the damped mass center of detections and $\lambda_G$ represents the scale associated with the Gaussian term approximating the detection terms;

$\vec{r}_j$ represents the locations of the searching system sensor where no detection has been made;

$N_M$ is the number of measurement locations;

$\lambda_u$ represents the scale of the Gaussian terms approximating the non-detection terms; and $Z_t$ is a normalization constant.

The lack of space perception coupled with the accumulation of positioning errors lead, preferably, to precautions being taken in relation to the amount of "memory" that the searching system should keep from its past. Hence, the damped center of mass can be expressed as follows:

$$\vec{r}_G = \frac{\sum_{i=1}^{G} \gamma^{G-i} \vec{r}(t_i)}{\sum_{i=1}^{G} \gamma^{G-i}}$$

where $\gamma<1$ and $\{t_i, i=1 \ldots G\}$ represents the times of the measurements.

As described above, the searching system is based on the use of the projection of a probability of the diffusion source position into a standardized form and on the evaluation of a free energy. Accordingly, to decide the direction to be taken after experiencing the self-generated path $\Theta_t$ (in view of user-defined constraints if any), a function of $P_t^M(\vec{r}_0|\Theta_t)$ is to be determined. The minimum value obtained from such a function of $P_t^M(\vec{r}_0|\Theta_t)$ according to one of a plurality of possible directions, is used to choose the direction to be taken.

Optimization based on entropy computation is known to be efficient (in particular, from EP 1,881,389). However, since it has been observed that entropy tends to shift the exploration versus exploitation balance towards exploration, another term has been added to reinforce maximum likelihood behavior and so shift the balance towards exploitation. Accordingly, a free energy can be expressed according to the following formula:

$$F_t(\Theta_t) = W_t(\Theta_t) + TS(\Theta_t)$$

where $W_t(\Theta_t)$ represents a working energy;
$S(\Theta_t)$ represents the Shannon entropy; and
T a temperature parameter that controls the relative value between these two elements.

Therefore, the free energy can be expressed as follows:

$$F_t(\Theta_t) = \iint_{|\vec{r}_0 - \vec{r}_G| \leq \frac{\lambda_G}{2}} d\vec{r}_0 P_t^M(\vec{r}_0 | \Theta_t) + T\left[-\iint d\vec{r}_0 P_t^M(\vec{r}_0 | \Theta_t) \log P_t^M(\vec{r}_0 | \Theta_t)\right]$$

When moving from the sensor position at time t, denoted $\vec{r}_t$, to a neighboring position corresponding to time t+dt, denoted $\vec{r}_{t+dt}$, the expected variation of the free energy is the sum of two terms, one accounting for the discovery of the source and the other one for its absence. This variation reads as follows:

$$\Delta F_t(\vec{r}_t \to \vec{r}_{t+dt} | \Theta_t) = P_t^M(\vec{r}_{t+dt}) \Delta F_t^{discovery} + (1 - P_t^M(\vec{r}_{t+dt})) \Delta F_t^{nothing}$$
$$= P_t^M(\vec{r}_{t+dt})[1 - F_t(\Theta_t)] + (1 - P_t^M(\vec{r}_{t+dt}))$$
$$[\rho_0(\vec{r}_{t+dt}) \Delta F_t^0(\Theta_t) + \rho_1(\vec{r}_{t+dt}) \Delta F_t^1(\Theta_t)]$$

where $P_t^M(\vec{r}_{t+dt})$ represents the probability that the source is at position $\vec{r}_{t+dt}$;
$F_t(\Theta_t)$ represents the free energy of the searcher at time t;
$F_{t+dt}(\Theta_t) = 1$ is the free energy if the source is found;
$[1 - P_t^M(\Theta_t)]$ is the probability that the source is not at position $\vec{r}_{t+dt}$;
$\rho_i(\vec{r}_{t+dt})$ represents the expected probability of having i detections; and
$\Delta F_t^i(\Theta_t)$ is the expected free energy variation if there were i detections.

According to the Poisson detection function, the expected probability of having i detections can be expressed as follows:

$$\rho_i(\vec{r}) = \frac{[(\vec{r})]^i e^{-h(\vec{r})}}{i!}$$

where $h(\vec{r})$ represents the expected average hit rate that can be expressed as follows:

$$h(\vec{r}) = \int d\vec{r}_0 R(\vec{r} | \vec{r}_0) P_t^M(\vec{r}_0)$$

where $R(\vec{r} | \vec{r}_0)$ is the rate of detection of the searching system if it is at the position and the source is at $\vec{r}_0$. This can be approximated using a Gaussian function.

The updating rule of $\vec{r}_G$, to avoid storing the hit positions, can be expressed as follows:

$$\vec{r}_{G+1} = \gamma \frac{1-\gamma^G}{1-\gamma^{G+1}} \vec{r}_G + \frac{1-\gamma}{1-\gamma^{G+1}} \vec{r}(t_{G+1})$$

In case of turbulent transport (e.g. wind), the updating procedure of $\vec{r}_G$ can be expressed as follows:

$$x_G = \frac{\sum_{i=1}^{G} \gamma(V)^{G-i} x(t_i)}{\sum_{i=1}^{G} \gamma(V)^{G-i}}$$

and $$y_G = y(t_G)$$

with the turbulent transport being oriented in the −y (minus y) direction (at time t), e.g. wind blowing in the −y direction, and $\gamma(V)$ is the damping factor decreasing with rising velocity.

Depending on the characteristics of the environment where the emitting source is to be found, the shape of $\gamma(V)$ may be chosen to better fit the characteristics of the detection. Linear dependency with a maximum velocity is found to be efficient. Obviously, if the turbulent transport direction varies with a similar time scale as the sensor is moved, the search becomes extremely difficult, and the updating procedure of $\vec{r}_G$ is preferably the one used in the turbulentless (e.g. windless) scheme. It is to be noted that in order to ensure that an emitting source will be found, the drift velocity information is underexploited. The symmetry of the distribution ensures that the searcher can go in the opposite direction to the turbulent transport (e.g. wind) if it has moved beyond the source position.

Drift velocity information processing can be improved as follows: after each detection, a random distance L is randomly generated from an exponential distribution of correlation length $L_T=\chi\lambda_e$ ($\chi$ being user-defined) and the sensor is moved according to distance L in the opposite direction to the turbulent transport such as wind (at the time). Conversely, to reinforce stability of the search for the rare (<1/500) searches where a sequence of detection with low probabilities happened (far from the source), the sensor is moved back to the last point (with the accumulated odometry error) where a detection has been made after a user-defined time without any detection. Finally, initial spiraling is made on an asymmetrical spiral which is more extended when going in the opposite direction to the turbulent transport (e.g. wind) than when going in the direction of the turbulent transport.

If the turbulent transport is expected not to change direction (or to change direction only slightly) during the search, asymmetry between turbulent transport direction and perpendicular direction can be added to $P_t^M(\vec{r}_0|\Theta_t)$ to reinforce turbulent transport information use.

If the constraint of always finding the source is removed, the efficiency of the search for the source can be improved. For example, reducing the choice of possible moving points to the ones in the opposite direction to the turbulent transport (e.g. wind) and diminishing the internal temperature T to reinforce information exploitation leads to fast searches when the searcher finds the source.

It is to be noted that all the terms involved in determining the direction to be taken after experiencing the self-generated path $\Theta_t$, i.e. $F_t(\Theta_t)$, $W_t(\Theta_t)$, $S(\Theta_t)$, $h_t(\vec{r}_t)$, and $\rho_t(\vec{r}_t)$, can be approximated so that they do not depend on $P_t^M(\vec{r}_0|\Theta_t)$, for example according to the following formulae:

$$W(\Theta_t) = \int\int_S d\vec{r}_0 P_t(\vec{r}_0|\Theta_t) = \frac{1}{Z_t}\left[\pi\left(\text{erf}\left(\frac{1}{2}\right)\lambda_G\right)^2 - \frac{1}{N_M}\sum_{j=N_t-N_M+1}^{N_t}\frac{\pi\lambda_G^2\lambda_u^2}{4(\lambda_G^2+\lambda_u^2)}e^{-\frac{\|\vec{r}_G-r_j\|}{(\lambda_G^2+\lambda_u^2)}}\Phi(x_j,x_G)\Phi(y_j,y_G)\right]$$

with S representing the integration domain that is defined here by $$|\vec{r}_0-\vec{r}_j|\leq\frac{\lambda}{2}$$

and where $$\Phi(x_j,x_G) = \text{erf}\left(\frac{-\lambda_d^2-2x_j\lambda_d+2x_G\lambda_d-\lambda_u^2}{2\lambda_u\sqrt{\lambda_G^2+\lambda_u^2}}\right) - \text{erf}\left(\frac{\lambda_d^2-2x_j\lambda_d+2x_G\lambda_d+\lambda_u^2}{2\lambda_u\sqrt{\lambda_G^2+\lambda_u^2}}\right)$$

$$S(\Theta_t) \approx \log(Z_t) + \frac{\pi}{2Z_t}(\lambda_G^2+\lambda_u^2) + \frac{\pi}{Z_t}\sum_{j=N_t-N_M+1}^{N_t} e^{-\frac{\|\vec{r}_G-r_j\|^2}{(\lambda_G^2+\lambda_u^2)}}$$

$$\left[\frac{\lambda_G^2+\lambda_u^2}{(\lambda_G^2+\lambda_u^2)} - \frac{\lambda_G\lambda_u(\lambda_G^3\lambda_u(x_G-x_i)^2+\lambda_G\lambda_u^3/2)}{(\lambda_G^2+\lambda_u^2)} - x\to y\right]$$

with the approximation $$\log\left(1-\frac{1}{N_M}\sum_{j=N_t-N_M+1}^{N_t} e^{-\frac{\|\vec{r}_0-r_j\|^2}{\lambda_u^2}}\right) \approx -\frac{1}{N_M}\sum_{j=N_t-N_M+1}^{N_t} e^{-\frac{\|\vec{r}_0-r_j\|^2}{\lambda_u^2}}$$

and where all the cross terms $$\frac{1}{N_M}\sum_{j=N_t-N_M+1}^{N_t} e^{-\frac{\|\vec{r}_0-r_j\|^2}{\lambda_u^2}} \times \frac{1}{N_M}\sum_{j=N_t-N_M+1}^{N_t} e^{-\frac{\|\vec{r}_0-r_j\|^2}{\lambda_u^2}}$$

have been neglected (mean field approximation); and $$h(\vec{r}) = \frac{\pi\kappa}{Z_t}\left(\frac{1}{2}\lambda_G^2 e^{-\frac{\|\vec{r}_G-r_j\|^2}{2\lambda_u^2}} - \frac{1}{N_M}\sum_{j=N_t-N_M+1}^{N_t}\frac{\lambda_G^2+\lambda_u^2}{(\lambda_G^2+2\lambda_u^2)}\Psi(x_G,x_j,x)\Psi(y_G,y_j,y)\right)$$

with the user defined factor $\kappa$ and $$\Psi(x_G,x_j,x) = e^{\frac{(-(x_G^2+x^2)(\lambda_G^2+\lambda_u^2)+\lambda_G^2(-2x_j^2+2x_Gx_j+2x_Gx\lambda_u^2))}{(\lambda_G^2+2\lambda_u^2)\lambda_G^2}}$$

It is also to be noted that such formulae can be expressed differently to optimize updates and to reduce required memory accesses. To that end, the standardized form of the probability field can be expressed as follows:

$$P_t^M(\vec{r}_0|\Theta_t) = \frac{e^{-\frac{|\vec{r}_0-\vec{r}_G|^2}{\lambda_G^2}}\left(1-\sum_{j=1}^{N_t}\rho^{N_t-j}e^{-\frac{|\vec{r}_0-\vec{r}_j|^2}{\lambda_G^2}}\right)}{Z_t} \text{ with } \rho<1$$

By defining $\Xi_t(\vec{r}_0|\Theta_t)$ as follows:

$$\Xi_t(\vec{r}_0|\Theta_t) = \sum_{j=1}^{N_t}\rho^{N_t-j}e^{-\frac{|\vec{r}_0-\vec{r}_j|^2}{\lambda_u^2}}$$

an updating rule may be expressed as follows:

$$\Xi_{t+dt}(\vec{r}_0|\Theta_{t+dt}) = \rho\Xi_t(\vec{r}_0|\Theta_t) + e^{-\frac{|\vec{r}_0-\vec{r}_{N+1}|^2}{\lambda_u^2}}$$

Similarly by defining $Z_t$ as follows:
$Z_t=\pi\lambda_G^2-\Gamma_t$ with $$\Gamma_t = \pi\frac{\lambda_G^2\lambda_u^2}{\lambda_G^2+\lambda_u^2}\sum_{j=1}^{N_t}\rho^{N_t-j}e^{-\frac{|\vec{r}_G-\vec{r}_j|^2}{\lambda_G^2+\lambda_u^2}}$$

and the following updating rules $$\Gamma_{t+dt} = \rho\Gamma_{t+dt} + \pi \frac{\lambda_G^2 \lambda_u^2}{\lambda_G^2 + \lambda_u^2} e^{-\frac{|\vec{r}_G - \vec{r}_{N+1}|^2}{\lambda_G^2 + \lambda_u^2}}$$

hence $$Z_{t+dt} = \pi \lambda_G^2 - \Gamma_{t+dt}.$$

Furthermore, the work energy becomes $$W(\Theta_t) = \frac{1}{Z_t}\left[\pi\left(\mathrm{erf}\left(\frac{1}{2}\right)\lambda_G\right)^2 - \sum_{j=1}^{N_t} \rho^{N_t-j} \frac{\pi \lambda_G^2 \lambda_u^2}{4(\lambda_G^2 + \lambda_u^2)} e^{-\frac{|\vec{r}_0 - \vec{r}_G|^2}{\lambda_G^2 + \lambda_u^2}} \Phi(x_j, x_G)\Phi(y_j, y_G)\right]$$

By defining $$\Omega_t = \sum_{j=1}^{N_t} \rho^{N_t-j} \frac{\pi \lambda_G^2 \lambda_u^2}{4(\lambda_G^2 + \lambda_u^2)} e^{-\frac{|\vec{r}_j - \vec{r}_G|^2}{\lambda_G^2 + \lambda_u^2}} \Phi(x_j, x_G)\Phi(y_j, y_G)$$

and the updating rule $$\Omega_{t+dt} \leftarrow \rho\Omega_t + \frac{\pi \lambda_G^2 \lambda_u^2}{4(\lambda_G^2 + \lambda_u^2)} e^{-\frac{|\vec{r}_{N+1} - \vec{r}_G|^2}{\lambda_G^2 + \lambda_u^2}} \Phi(x_{N+1}, x_G)\Phi(y_{N+1}, y_G)$$

hence $$W(\Theta_{t+dt}) = \frac{1}{Z_{t+dt}}\left[\pi\left(\mathrm{erf}\left(\frac{1}{2}\right)\lambda_G\right)^2 - \Omega_{t+dt}\right]$$

and $$S(\Theta_t) \approx \log(Z_t) + \frac{\pi}{2Z_t}(\lambda_G^2 + \lambda_u^2) +$$

$$\frac{\pi}{Z_t}\sum_{i=1}^{N_t}\rho^{N_t-i}e^{-\frac{|\vec{r}_G-\vec{r}_i|^2}{\lambda_G^2+\lambda_u^2}}\left[\frac{\lambda_G^2\lambda_u^2}{\lambda_G^2+\lambda_u^2} - \frac{\lambda_G\lambda_u(\lambda_G^3\lambda_u(x_G-x_i)^2+\lambda_G\lambda_u^3/2)}{(\lambda_G^2+\lambda_u^2)^2} - \right.$$

$$\left.\frac{\lambda_G\lambda_u(\lambda_G^3\lambda_u(y_G-y_i)^2+\lambda_G\lambda_u^3/2)}{(\lambda_G^2+\lambda_u^2)^2}\right]$$

with $$\Psi_t = \sum_{i=1}^{N_t}\rho^{N_t-i}e^{-\frac{|\vec{r}_G-\vec{r}_i|^2}{\lambda_G^2+\lambda_u^2}}\left[\frac{\lambda_G^2\lambda_u^2}{\lambda_G^2+\lambda_u^2} - \frac{\lambda_G\lambda_u(\lambda_G^3\lambda_u(x_G-x_i)^2+\lambda_G\lambda_u^3/2)}{(\lambda_G^2+\lambda_u^2)^2} - \right.$$

$$\left.\frac{\lambda_G\lambda_u(\lambda_G^3\lambda_u(y_G-y_i)^2+\lambda_G\lambda_u^3/2)}{(\lambda_G^2+\lambda_u^2)^2}\right]$$

the updating rule $$\Psi_{t+dt} = \rho\Psi_{t+dt} + e^{-\frac{|\vec{r}_G-\vec{r}_{N+1}|^2}{\lambda_G^2+\lambda_u^2}}\left[\frac{\lambda_G^2\lambda_u^2}{\lambda_G^2+\lambda_u^2} - \Theta(x_G, x_{N+1}) - \Theta(y_G, y_{N+1})\right]$$

with $$\Theta(x_G, x_{N+1}) = \frac{\lambda_G\lambda_u(\lambda_G^3\lambda_u(x_G - x_{N+1})^2 + \lambda_G\lambda_u^3/2)}{(\lambda_G^2 + \lambda_u^2)^2}$$

leading to $$S(\Theta_{t+dt}) \approx \log(Z_{t+dt}) + \frac{\pi}{2Z_{t+dt}}(\lambda_G^2 + \lambda_u^2) + \frac{\pi}{Z_{t+dt}}\Psi_{t+dt}.$$

It is to be noted that for both $\Omega_t$ and $\Psi_t$ an approximation is preferably made in the updating rule: the function $\Phi$ depends on $\vec{r}_G$ which varies in time but the updating rules assume that $\vec{r}_G$ does not vary for the terms earlier in time.

Finally, $$h_t(\vec{r}) = \frac{\pi\kappa}{Z_t}\left(\frac{1}{2}\lambda_G^2 e^{-\frac{|\vec{r}_G-\vec{r}|^2}{2\lambda_G^2}} - A_t\right)$$

with $$A_t = \sum_{j=1}^{N_t}\rho^{N_t-j}\frac{\lambda_G^2\lambda_u^2}{2\lambda_u^2 + \lambda_G^2}\Omega(x_G, x, x_{N+1})\Omega(y_G, y, y_{N+1})$$

with $$\Omega(x_G, x, x_{N+1}) = e^{\frac{[-x_G^2(\lambda_u^2+\lambda_G^2)-x^2(\lambda_u^2+\lambda_G^2)+\lambda_G^2(-2x_{N+1}^2+2x_Gx_{N+1}+2xx_{N+1})+2x_Gx\lambda_u^2]}{(2\lambda_u^2+\lambda_G^2)+\lambda_G^2}}$$

and the following updating rule $$A_{t+dt} = \rho A_t + \frac{\lambda_G^2\lambda_u^2}{2\lambda_u^2 + \lambda_G^2}\Omega(x_G, x, x_{N+1})\Omega(y_G, y, y_{N+1})$$

leading to $$h_{t+dt} = \frac{\pi\kappa}{Z_{t+dt}}\left(\frac{1}{2}\lambda_G^2 e^{-\frac{|\vec{r}_G-\vec{r}|^2}{2\lambda_G^2}} - A_{t+dt}\right)$$

Accordingly, the direction to be taken can be computed easily without huge resources.

During the search, two processes ought to be balanced: exploration of the environment to get more information on the localization of the emitting source and exploitation of the already accumulated information.

In Infotaxis, as disclosed in particular in EP 1,881,389, the entropy is used to balance exploration and exploitation. Based on the reliable inference of the source position distribution $P_t(\vec{r}_0)$, the balance is efficiently managed with a clear advantage towards exploration.

According to a particular embodiment, information accessible from $P_t^M(\vec{r}_0|\Theta_t)$ is only partially reliable since the searching system has no exact access to the sensor position and the detection process may not correspond to the one used in the model used. The use of the working energy $W_t(\Theta_t)$ allows reinforcement of the maximum likelihood behavior and the temperature T allows the balance to be shifted between exploration and exploitation. It is to be noted that both exploration and exploitation are present in the entropy $S(\Theta_t)$ where mostly exploitation is present in the working energy $W_t(\Theta_t)$. This allows the temperature to actively control the balance. Furthermore, the working energy $W_t(\Theta_t)$ prevents the self-trapping behavior observed during simulations performed for high temperatures (T>5), when a large number of detections has been made far from (rare) and close to the source.

It is to be noted that at short initial distances (between the sensor and the emitting source), the use of a low temperature value is more efficient because the working energy $W_t(\Theta_t)$, which favors maximum likelihood behavior, has more influence on the decision process than at high temperature. As the initial distance rises, the optimum temperature rises with a flattening of the mean search time-temperature curve.

According to a particular embodiment, the sensor is moved after an initial detection. The initial movement is preferably defined as an Archimedean spiral. Such an Archimedean spiral movement is preferably used until a second detection is made. In case of turbulent transport, the initial spiral is preferably asymmetrical, with the spiral being wider in the opposite direction to the turbulent transport than in its direction.

Still according to a particular embodiment, a linear motion in a random direction may be chosen if the algorithm results in a decision of not moving the sensor.

Still in a particular embodiment, the memory of the searching system that is used to store previous detections may be reset when numerous detections have been made, after a user-defined time. Such an embodiment is particularly adapted to the case in which the sensor is initially located far from the source and hence reaches the vicinity of the source with numerous detections. Memory reset allows the balance of exploration/exploitation to shift back to exploration.

According to a particular embodiment, several independent mobile sensors, for example several intelligent mobile robots, are used to locate one or several emitting sources. The architecture and the features of these mobile sensors may be similar to those described above.

If the mobile sensors are still unable to determine their position accurately in the searching space and cannot correct odometry error, they are provided with communication means so as to transmit and/or receive data, in particular measurements of emission propagation and/or relative position information. Such data can be transmitted and/or received on a regular basis whatever the relative position of robots is or on a regular basis only if the robots are close to each other.

For the sake of illustration, two robots can locate each other using ultrasound sensors, sonars, cameras, and the like. The detection can be made by using local sensors or via a central computer able to communicate with the robots. Alternatively, all the robots are provided with their mutual initial positions, these positions being therefore known at least approximately by each robot.

According to this embodiment, the mobile sensors (or robots) move along self-generated paths $\Theta_i^t$ i∈(1 ... Ns), with $N_s$ representing the number of robots. The latter have to decide their future paths based on information accumulated into paths $\Theta_i^t$. More precisely, each of the robots, moving in a medium where localization (SLAM, Simultaneous Localization And Mapping) is either difficult or impossible, takes individual decisions based on a global path $\Theta_t$ and estimates its position from uncorrected path integration. As a consequence, all robots accumulate odometry errors as they search for the emitting source(s) and have no direct way to correct them.

The standardized projected probability that an emitting source is located in $\vec{r}_0$ knowing path $\Theta_t$ can be defined as follows:

$$P_t^M(\vec{r}_0 | \Theta_t) = \frac{e^{-\frac{\|\vec{r}_0 - \vec{r}_G^{N_s}\|^2}{\lambda_G^2}} \left( -\frac{1}{N_M} \sum_{k=1}^{N_s} \sum_{j=N_t-[\frac{(N_M+1)}{N_s}]}^{N_s} e^{-\frac{\|\vec{r}_0 - \vec{r}_j^k\|^2}{\lambda_u^2}} \right)}{Z_t}$$

where $\vec{r}_G^{N_s}$ represents the damped mass center of detections made by all the robots and $\lambda_G$ represents the scale associated with the Gaussian term approximating the detection terms;

$\vec{r}_j^k$ represents the locations of the robot having index k (i.e. the searching system sensor having index k) where no detection has been made;

$N_M$ is the number of measurement locations;

$\lambda_u$ represents the scale of the Gaussian terms approximating the non-detection terms; and $Z_t$ is a normalization constant.

Again, it is noted that the lack of space perception coupled with the accumulation of positioning errors lead, preferably, to precautions being taken in relation to the amount of "memory" that the searching system should keep from its past.

Like the damped centre of mass expressed for the detections made by a single robot, the damped mass center of detections made by all the robots can be expressed as follows:

$$\vec{r}_G^{N_s} = \frac{\sum_{i=1}^{G} \gamma^{G-i} \vec{r(t_i)}}{\sum_{i=1}^{G} \gamma^{G-i}}$$

where $\gamma<1$, $\vec{r(t_i)}$ is the position of one robot which made the detection at time $t_i$, and $\{t_i, i=1 ... G\}$ represents the times of the measurements ordered from the most recent detections to the oldest detections.

In such a swarm searching process, robots share information regarding their trajectories. More precisely, the robots share information regarding noisy trajectories that are determined without odometry error corrections (true positions may significantly differ from those that are shared).

If robots cannot share information on a regular basis (e.g. if robots are far away from each other), the standardized projected probability $P_t^M(\vec{r}_0|\Theta_t)$ is updated as a function of the damped mass center of detections made by all the robots and of locations of the robot having index k where no detection has been made if such information is available (i.e. when robots can exchange information) or as a function of the damped mass center of detections made by the robot and of its locations where no detection has been made (i.e. when robots cannot exchange information).

To determine its next position, each robot minimizes the free energy $F_t(\Theta_t)$ as described above. As mentioned above, each robot takes individual decisions to generate its own path and information is shared through the part of the path that each robot shares.

Figure 4A:
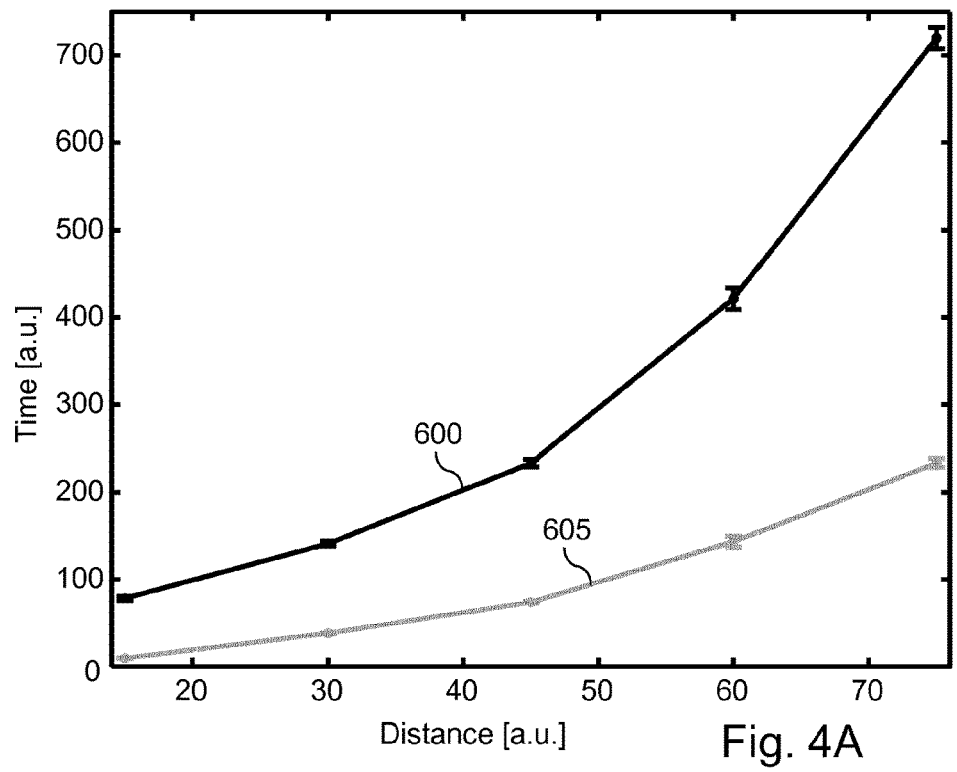
FIGS. 4a and 4b, illustrates an advantage of using several robots to locate one or several emitting sources.
Figure 4B:
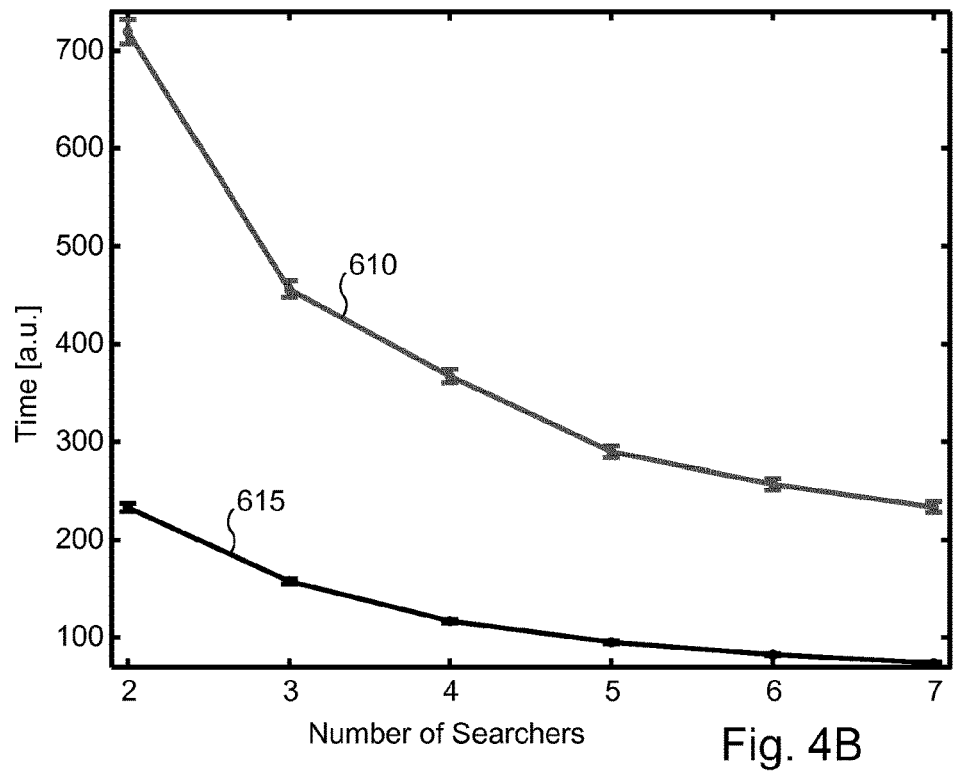

FIG. 4, comprising FIGS. 4a and 4b, illustrates an advantage of using several robots to locate one or several emitting sources.

FIG. 4a illustrates the variation of the average searching time as a function of the average distance between the robots and the centers of two emitting sources (which are distant from each other by distance λ=30 a.u.) and as a function of the number of robots used. Curve 600 represents the variation of the average searching time when two robots are used and curve 605 represents the variation of the average searching time when seven robots are used.

FIG. 4b illustrates the variation of the average searching time as a function of the number of robots and as a function of the distance between the robots and the centers of two emitting sources (which are distant from each other by distance λ=30 a.u.). Curve 610 represents the variation of the average searching time when the distance between the robots and the centers of two emitting sources is equal to 75 a.u. and curve 615 represents the variation of the average searching time when the distance between the robots and the centers of two emitting sources is equal to 45 a.u.

Embodiments of the invention may be used for robotic searches in random environments, especially when localization is either unachievable or too complicated to be achieved continuously. This could also be named blind robot searches. According to specific wording, embodiments allow searches when SLAM is difficult to achieve.

Embodiments may also be used for searches in complex environments with sparse unreliable signals. For example searches for planes or boats in oceans by using detections of a remaining signal sporadically emitted and the local bathymetry.

Embodiments of the invention also find direct applications in reinforcement learning and machine learning. Examples of such applications concern search problems where a balance has to be found between exploration and exploitation. Other applications are linked to quantitative economy that can be expressed, in particular, as tree decision problems where a balance between exploration and exploitation is to be achieved.

Depending on the applications, user-defined constraints can be associated with the self-generated path. For the sake of illustration, if the system of the invention is used for locating a signal source along wires, the self-generated path is limited to the wire network.

Naturally, in order to satisfy local and specific requirements, a person skilled in the art may apply to the solution described above many modifications and alterations all of which, however, are included within the scope of protection of the invention as defined by the following claims.

The invention claimed is:

1. A method for locating an emitting source of which a measurement of emission propagation at a different location from that of the emitting source can be obtained from that different location, in a searching space, lacking space perception, using a mobile sensor configured to obtain emission propagation measurements, the sensor being mobile along a self-generated path, the method comprising:

obtaining an emission propagation measurement from the mobile sensor at the mobile sensor location;

for a plurality of possible next locations of the mobile sensor, computing a free energy variation for moving the sensor from its current location to each of the plurality of possible next locations, the free energy being computed as a function of a standardized projected probability field of the location of the emitting source based on previous emission propagation measurements obtained along the self-generated path without space perception;

determining a minimum free energy variation value amongst the computed free energy variations;

identifying the location associated with the determined minimum free energy variation as being the next location of the mobile sensor;

moving the mobile sensor to the identified next location of the mobile sensor, wherein a measurement of emission propagation characterizes detecting or not detecting emission of the emitting source and wherein the standardized projected probability field of the location of the emitting source, representing the probability $P_t^M(\vec{r}_o|\Theta_t)$ that the emitting source is located at location $\vec{r}_o$, knowing path $\Theta_t$, can be expressed with the following formula:

$$P_t^M(\vec{r}_o|\Theta_t) = \frac{e^{-\frac{\|\vec{r}_o-\vec{r}_G\|^2}{\lambda_G^2}}\left(1 - \frac{1}{N_M}\sum_{j=N_t-N_M+1}^{N_t} e^{-\frac{\|\vec{r}_o-\vec{r}_j\|^2}{\lambda_u^2}}\right)}{Z_t}$$

where $\vec{r}_G$ represents a damped mass center of previous locations where emission of the emitting source has been detected and $\lambda_G$ represents a scale associated with a Gaussian term approximating terms associated with detection of emission of the emitting source;

$\vec{r}_j$ represents the locations of the searching system sensor where emission of the emitting source has not been detected;

$N_m$ is the number of locations where measurements have been obtained;

$\lambda_u$ represents a scale of a Gaussian term approximating terms associated with absence of detection of emission of the emitting source; and $Z_t$ is a normalization constant.

2. The method according to claim 1, wherein the free energy variation is computed as a function of a first element that favors exploration of the searching space and as a function of a second element that favors exploitation of previous emission propagation measurements obtained along the self-generated path, the first and second elements being weighted in relation to each other.

3. The method according to claim 1, further comprising determining whether the current sensor location or the next location of the mobile sensor corresponds to the location of the emitting source.

4. The method according to claim 3, wherein the obtaining an emission propagation measurement, computing a free energy variation, determining a minimum free energy variation value, identifying the next location of the mobile sensor, and determining whether the current sensor location or the next location of the mobile sensor corresponds to the location of the emitting source are repeated until the location of the emitting source is located.

5. The method according to claim 1, further comprising comparing the determined minimum free energy variation value with a predetermined threshold, the next location of the mobile sensor being identified as the location associated with the determined minimum free energy variation or as the current sensor location as a function of the result of the comparison.

6. The method according to claim 1, further comprising storing the obtained emission propagation measurement in memory along with the current mobile sensor location.

7. The method according to claim 1, wherein the obtaining an emission propagation measurement from the mobile sensor at the mobile sensor location further comprises obtaining at least an emission propagation measurement from at least a second mobile sensor, different from the mobile sensor, at the location of the at least a second mobile sensor, the at least a second mobile sensor being configured to obtain emission propagation measurements, the at least a second mobile sensor being mobile along at least a second self-generated path, the free energy being computed as a function of the standardized projected probability field of the location of the emitting source based on previous emission propagation measurements obtained along the self-generated path and on at least a previous emission propagation measurement obtained along the at least a second self-generated path.

8. The method according to claim 1, wherein the emitting source is a source of particles, molecules, or fragments of molecules.

9. The method according to claim 1, wherein the emitting source is a heat source.

10. The method according to claim 1, wherein the emitting source is a source of data, the sensor being responsive to data patterns.

11. A non-transitory computer-readable storage medium storing instructions of a computer program for implementing the method according to claim 1.

12. An apparatus or a set of apparatus comprising means adapted for carrying out each step of the method according to claim 1.

13. The apparatus or the set of apparatus of claim 12, comprising first means embedding the mobile sensor, the first means being mobile in the search space, and second means for computing the free energy variation, determining a minimum free energy variation value, and identifying the next location of the mobile sensor, the first and second means comprising means for exchanging data with each other.

14. A method for locating an emitting source of which a measurement of emission propagation at a different location from that of the emitting source can be obtained from that different location, in a searching space, lacking space perception, using a mobile sensor configured to obtain emission propagation measurements, the sensor being mobile along a self-generated path, the method comprising:
obtaining an emission propagation measurement from the mobile sensor at the mobile sensor location;
for a plurality of possible next locations of the mobile sensor, computing a free energy variation for moving the sensor from its current location to each of the plurality of possible next locations, the free energy being computed as a function of a standardized projected probability field of the location of the emitting source based on previous emission propagation measurements obtained along the self-generated path without space perception;
determining a minimum free energy variation value amongst the computed free energy variations;
identifying the location associated with the determined minimum free energy variation as being the next location of the mobile sensor; and
moving the mobile sensor to the identified next location of the mobile sensor,
wherein the standardized projected probability field of the location of the emitting source, representing the probability $P_t^M(\vec{r}_0|\Theta_t)$ that the emitting source is located at location $\vec{r}_0$, knowing path $\Theta_t$, can be expressed with the following formula:

$$P_t^M(\vec{r}_0 \mid \Theta_t) = \frac{e^{-\frac{\left\|\vec{r}_0 - \vec{r}_G^{N_s}\right\|^2}{\lambda_G^2}} \left( -\frac{1}{N_M} \sum_{k=1}^{N_s} \sum_{j=N_t - \left[\frac{(N_M+1)}{N_s}\right]}^{N_s} e^{-\frac{\left\|\vec{r}_0 - \vec{r}_j^k\right\|^2}{\lambda_u^2}} \right)}{Z_t}$$

where
$\vec{r}_G^{N_s}$ represents a damped mass center of previous locations where emission of the emitting source has been detected by the mobile sensor and the at least a second mobile sensor and $\lambda_G$ represents a scale associated with a Gaussian term approximating terms associated with detection of emission of the emitting source;
$\vec{r}_j^k$ represents the locations of a searching system sensor having index k where emission of the emitting source has not been detected;
$N_M$ is the number of locations where measurements have been obtained;
$\lambda_u$ represents a scale of a Gaussian term approximating terms associated with absence of detection of emission of the emitting source; and
$Z_t$ is a normalization constant.

* * * * *